United States Patent [19]

Pasini et al.

[11] Patent Number: 4,732,893

[45] Date of Patent: Mar. 22, 1988

[54] AMINO-ANTHRACENEDIONES-PLATINUM COMPLEXES USEFUL AS ANTICANCER COMPOUNDS

[75] Inventors: Alessandro Pasini; Franco Zunino; Odoardo Tofanetti; Carmelo A. Gandolfi; Sergio Tongnella, all of Milan, Italy

[73] Assignee: Boehringer Biochemia Robin S.p.A., Milan, Italy

[21] Appl. No.: 761,787

[22] Filed: Aug. 2, 1985

[30] Foreign Application Priority Data

Aug. 3, 1984 [IT] Italy ............................... 22224 A/84
Jun. 27, 1985 [IT] Italy ............................... 21324 A/85

[51] Int. Cl.$^4$ ............................................. C07F 15/00
[52] U.S. Cl. ..................... 514/185; 260/366; 556/137; 544/64; 546/10; 548/108; 548/402
[58] Field of Search ............. 556/137; 260/366; 546/10; 544/64; 548/108, 402; 514/185

[56] References Cited

U.S. PATENT DOCUMENTS

| | | | |
|---|---|---|---|
| 2,166,076 | 7/1939 | Rosenblatt | 556/137 |
| 3,876,675 | 4/1975 | Trofimenko | 556/137 X |
| 4,197,249 | 4/1980 | Murdock et al. | 260/380 |
| 4,203,912 | 5/1980 | Hydes et al. | 556/137 X |
| 4,250,189 | 2/1981 | Hydes et al. | 556/137 X |
| 4,283,342 | 8/1981 | Yolles | 260/366 X |
| 4,296,030 | 10/1981 | Lang, Jr. et al. | 260/366 X |
| 4,393,007 | 7/1983 | Priester et al. | 260/366 X |
| 4,588,831 | 5/1986 | Sagredos et al. | 260/366 X |

FOREIGN PATENT DOCUMENTS 0037486 10/1981 European Pat. Off. .

OTHER PUBLICATIONS

Van Duuren et al., J. of Medicinal Chem. 21 (1) pp. 26 to 31 (1978).
Papageorgiou et al., Can. J. Chem. 60 pp. 2477 to 2483 (1982).
Chemical Abstracts 101 182588g (1984).

Primary Examiner—Helen M. S. Sneed
Attorney, Agent, or Firm—Murray and Whisenhunt

[57] ABSTRACT

Platinum complex having formula (I)

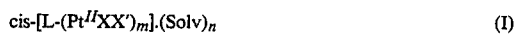

$$\text{cis-}[L\text{-}(Pt^{II}XX')_m]\cdot(Solv)_n \qquad (I)$$

wherein
m is 1 or 2;
X and X', which are the same or different, are Cl, OH, $CH_3SOCH_3\cdot Cl$ or $CH_3SOCH_3\cdot H_2O$;
L is a bidentate ligand of formula II

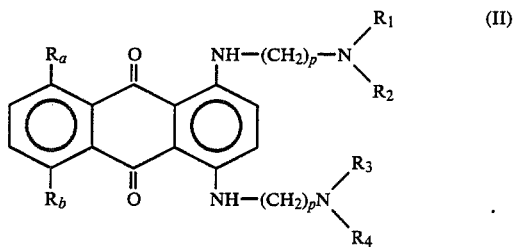

Solv. represents the crystallization solvents and m is zero, 0.5 or an integer from 1 to 6,
are described.

The compounds I are useful in therapy as antitumoral agents.

14 Claims, No Drawings

AMINO-ANTHRACENEDIONES-PLATINUM COMPLEXES USEFUL AS ANTICANCER COMPOUNDS

The present invention relates to novel platinum complexes, to a method for their preparation and to pharmaceutical and veterinary compositions containing them.

The compounds of the invention are cis-platinum$^{II}$ complexes of formula I $$\text{cis-}[L\text{-}(Pt^{II}XX')_m]\cdot(Solv)_n \qquad (I)$$

wherein
X and X', which can be the same or different, are a ligand selected from the group consisting of Cl, OH, $CH_3SOCH_3$.Cl, $CH_3SOCH_3$.OH;
m is an integer from 1 to 2;
n is zero or ½ or an integer from 1 to 6;
solv represents a crystallization solvent selected from the group consisting of water, a lower $C_1$-$C_5$ alcohol, acetonitrile or ethylacetate and
L is a bidentate ligand selected from the group of an 1,4-diamino-9,10-anthracenedione of formula II

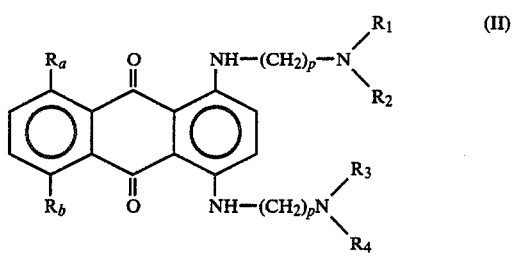

wherein each of
$R_a$ and $R_b$, which are the same or different, are hydrogen or hydroxy;
$R_1$, $R_2$, $R_3$ and $R_4$, which are the same or different, are hydrogen, $C_1$-$C_5$ lower alkyl and —$(CH_2)$-$_{p1}$—OH;
p and $p_1$ are, independently, the integer 2 or 3; or one or both of $R_1$, $R_2$ and $R_3$, $R_4$ respectively, taken together with the nitrogen atom to which they are connected, form an heterocyclic ring having formula

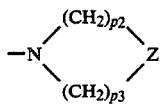

which are the same or different, wherein Z is —$CH_2$— or O, while $p_2$ and $p_3$ are independently 1 or 2; and a salt of said ligand L with pharmaceutically, nontoxic acceptable acids.

Pharmaceutically useful salts of the ligand L are those with monovalent inorganic acids such as hydrogen chloride, hydrogen bromide, hydrogen iodide and with organic acids such as acetic, succinic, tartaric and fumaric acids.

The compounds of the invention of formula I are prepared by mixing a solution of the ligand L of formula II, either in form of free base or of salt, in a suitable solvent with a solution of a platinum$^{II}$ compound selected from the group of potassium chloroplatinate ($K_2PtCl_4$) and dichloroplatinum acetonitrile [$PtCl_2(CH_3CN)_2$] in a suitable solvent, crystallizing che compounds of the invention of formula Ia $$\text{cis-}[L\text{-}(Pt^{II}X_2')_m]\cdot(Solv)_n \qquad (Ia)$$

wherein L, m, solv, n are as above defined and X' is a chlorine atom. The compounds of formula Ia are then optionally reacted with water in a suitable medium to give the compounds of formula Ib $$\text{cis-}[L\text{-}(Pt^{II}X'X'')_m]\cdot(Solv)_n \qquad (Ib)$$

wherein X', L, m, Solv, n are as above defined and X" is OH and, finally, if desired, the compounds Ia and Ib are finally reacted with dimethyl sulphoxide, obtaining therefore the compounds according to the invention.

When the ligand is in salt form, the compounds of the invention of formula I are also salts and thus m is 1; these salts, if desired, can be converted to neutral complexes by treatment with equimolecular amount of a base.

If desired, neutral complexes of the formula I wherein m is the integer 1, may be converted in the salt form by treatment with stoichiometric amount of a pharmaceutically, non-toxic acceptable acids.

When the ligand L is in the free base form, the complexes of the invention of formula I are also no-charged complexes (i.e. neutral complexes) and m is 1 or 2.

Complexes where one or two platinum atoms are coordinating a single mole of the ligand L, as free base, are obtained using different molar ratio between ligand and the reagents, i.e. one or more moles of a reagent such as potassium tetrachloroplatinate or $[PtCL_2.(CH_3CN)_2]$.

Preferred solvents are water, ethanol and $C_1$-$C_3$ lower alcohols, acetonitrile, dimethylformamide, formamide, dimethylacetamide and their mixture. The solutions of ligands and reagents are preferably mixed at temperatures ranging from $-10°$ C. up to about the solvent reflux temperature. The preferred temperature is the room temperature.

The reaction time ranges from few minutes to several days, but usually it does not exceed few hours and often few minutes are sufficient to complete the reaction.

Aquo complexes of formula Ib are obtained after prolonged treatment, at temperatures between freezing and boiling of the water, and preferably at room temperature, with water of a compound of formula Ia or from aqueous solutions of said compounds by slow exchange of the Cl ligand with the OH ligand. Compounds of formula Ib are also obtained by precipitation with $C_1$-$C_4$ lower alcohols from aqueous solutions of said compounds.

The complexes of the invention of formula Ia, Ib are characterized by a great solubility in dimethylsulphoxide (DMSO). After instant dilution with water of said concentrated solutions in DMSO, stable solutions of the complexes of the invention of formulae I, Ib in water are obtained.

Whenever solutions of the complexes of the invention Ia, Ib in DMSO are kept for a prolonged time, from few tens of minute to few days, at temperatures of e.g. 15°-40° C., preferably at room temperature, but most preferably for few hours at room temperature, insertion of 1 to 2 moles of DMSO, coordinated at the platinum atom, occurs in the complex.

The complexes of formula I wherein at least one of X is $CH_3SOCH_3$. Cl or $CH_3SOCH_3$.OH are then isolated, for example, by DMSO evaporation or by precipitation with a suitable solvent and subsequent crystallization.

The excess DMSO is generally removed by vacuum evaporation. Said reactions and operations are preferably carried out under an inert gas atmosphere.

The compounds of the invention, wherein the labile ligand contains one or two DMSO moles per platinum atom are soluble in water and do not require co-solvents for their dissolution in water.

Preferred compounds of the invention are those wherein m is 1. Most preferred compounds of the invention are those wherein m is 1 and the ligand of formula II is salified with almost one equivalent of one monovalent acid and preferably with two equivalents of said acids. Very often, these complexes are on their side characterized by a fairly good solubility in water.

Particularly preferred compounds of the invention are the compounds of formula cis-[L-PtCl$_2$)]·2HCl·(Solv)$_n$ and cis-[L-Pt(DMSO)$_2$Cl$_2$]·2HCl·(Solv)$_n$ wherein the ligand L, solvent and n are selected in the group consisting of:
1,4-bis-[2-(2-hydroxyethylamino)ethylamino]-5,8-dihydroxy-9,10-anthracenedione (H$_2$O)$_1$;
1,4-bis-[2-(2-hydroxyethylamino)ethylamino]-9,10-antracenedione (H$_2$O)$_1$;
1,4-bis-(2-aminoethylamino)-9,10-anthracenedione-(ethanol)$_{0.5}$;
1,4-bis-(2-aminoethylamino)-5,8-dihydroxy-9,10-anthracenedione (H$_2$O)$_1$;
1,4-bis-(morpholino-ethylamino)-5,8-dihydroxy-9,10-anthracenedione (Solv)$_o$;
1,4-bis-[2-(2-hydroxypropylamino)ethylamino]-5,8-dihydroxy-9,10-anthracenedione (H$_2$O)$_1$;
1,4-bis-[(2-hydroxyethylamino)propyl]-5,8-dihydroxy-9,10-anthracenedione;
1,4-bis-[2-(N-piperidyl)ethylamino]-9,10-anthracenedione (H$_2$O)$_1$;
1,4-bis-[2-(N-pyrrolidyl)ethylamino]-5,8-dihydroxy-9,10-anthracenedione;
1,4-bis-[2-(N-propylamino)ethylamino]-5,8-dihydroxy-9,10-anthracenedione (H$_2$O)$_1$;
cis-[L-Pt-ClOH]·2HCl·H$_2$O or
cis-[L-Pt(DMSO)$_2$ClOH]2HCl·H$_2$O
wherein the ligand L is selected in the group consisting of
1,4-bis-[[2-(2-hydroxyethyl)amino]ethylamino]-9,10-anthracenedione:
1,4-bis-[[2-[2-hydroxyethyl]amino]ethyl]amino]-5,8-dihydroxy-9,10-anthracenedione cis-[L-Pt-Cl$_2$]·H$_2$O wherein the ligand L is
1,4-bis-[[2-[2-hydroxyethyl]amino]ethyl]amino]-9,10-anthracenedione.

The ligand L of formula II are known compounds and they are prepared according to well known methods, see for example R. K. Y. Zee-Cheng et al. J. Med. Chem. 21, 291, 1978; K. C. Murdock et al. J. Med. Chem. 22, 1024, 1979; R. K. Y. Zee-Cheng et al. J. Med. Chem. 22, 501, 1979; R. K. Y. Zee-cheng et al. Drugs of the future, 8, 229, 1983 and references cited herein.

The remarkable biological activity of Pt$^{II}$ and Pt$^{IV}$ complexes as antitumoral agents, after the amino Pt$^{II}$ complexes have been discovered by Rosemberg (B. Rosemberg et al., Nature 205, 695, 1965) as powerful anticancer drugs, is well known. The antineoplastic activity of said complexes has been demonstrated in several animals affected by experimental tumors. These complexes inhibit tumor such as ascitic leukemia, Walker-256 carcino sarcoma, mammary tumors induced by dimethylbenzanthracene and ascitic melanoma B-16. Among these compounds, cis-diaminodichloroplatinum$^{II}$ (cis-DDP), is one of the best investigated agents, and it is used in the clinical practice.

Other platinum$^{II}$ complexes have also been successfully investigated in animal tests: recent advances are reported in "Platinum, Gold and other metal chemotherapeutic agents—Chemistry and Biochemistry" edited by S. J. Lippard, Am. Chem. Soc., Washington, D.C., 1983.

Cis-platinum$^{II}$ complexes currently investigated have the following formula

wherein A represents a carrier ligand, usually a nitrogen residue of the amine kind. Said ligand can be monodentate (NH$_3$, R—NH$_2$, R—NH—R) or bidentate, such as 1,2-diaminoethane, whereas X is monodentate or a bidentate leaving group such as chlorine or malonate, respectively.

The function of the carrier ligand is supposed to influence the activity of the whole complex through the steric and electronic effects of the carrier from which the whole basic nature of the complex depends. On the other hand, the leaving group could influence the hydrolysis of the complex and then its survival in biological fluids (see for example. "Platinum complexes, a new class of antineoplastic agents F. C. M. Leh and W. Wolf, J. Pharmac. Sc., 65, 315, 1976).

The leaving group probably influences the ability of the whole complex to reach unchanged the site of action. It seems also definitively stated that the carrier ligand is firmly bound to the platinum atom until the site of action is reached (see for example Caradonna et al., "Platinum coordinate complexes", pag. 14 in M.P. Hacker et al., N. Nihoff publ. Boston, 1984).

In the particular case of cis-platin, its activity is well demonstrated in the treatment of genito-urinary tumors, head and neck cancer, osteogenic sarcoma. Clinical observations continue to confirm the effectiveness of said compound against a number of human tumors, often when used in combination with other chemotherapeutic agents. In account of the serious side effects such as gastrointestinal (nausea and vomiting often severe and prolungated), renal (dose-limiting renal insufficiency), hematological, neurological (ototoxicity) complications, there is the need to make available new platinum derivatives with better therapeutic indexes and/or with a broader spectrum of actions in comparison with the parent compound.

On the other hand, clinical experiences with platinum$^{II}$ complexes, show that, similarly to other chemotherapeutic agents already used in the antineoplastic therapy, the platinum$^{II}$ complexes are sometimes devoid of specificity and, as a consequence of said reduced specificity combined with poor solubility and diffusibility of the drug in the biological fluids, a great incidence of side effects and poor results are often observed.

The entity of the side effects limit the maximum dosage which can be administered for each treatment, preventing thereby a complete destruction of the tumoral mass and of methastasis.

It has now been found that the complexes of platinum$^{II}$ having formula I are endowed with unexpected higher cytotoxic effect when compared with currently known cis-platinum$^{II}$ complexes. The compounds according to the invention, tested at relatively higher dosage levels, cause long-term survival of the treated animals, affected from tumors.

According to the invention, an amine-alkylamine-anthracenedione residue is the chemical substructure of the carrier ligand influencing the electronic and steric requirements of the complex and the overall basicity of the molecule.

It is also well known (see for example R. J. Adamson, "Recent development in cancer chemotherapy", Rargev, Basel, 1973, pp. 402-410) the hypothesis that, in many anticancer antibiotic molecules, a pharmacophore unit is present, which is responsible for a common transport system into neoplastic cells, where the compounds can then exert their biological action against the target cells. This pharmacophore unit is constituted by a particular atomic arrangement consisting of three electronegative atoms (each containing at least one lone pair of electrons), one nitrogen and two oxygen atoms, which form a triangular pattern and are separated one another at appropriate interatomic distances, namely O—O 3 ÅA; O—N 6 ÅA; O—N 8 ÅA.

The high activity of the compounds of the invention together with unexpected long-term survival of the treated animals may be probably due to the peculiar carrier characteristics of the ligand L of the compounds of the invention.

The activity seems to be due to the nature and properties of the nitrogen carrier, independently if the ligand L itself is endowed or not with relevant antineoplastic activity.

In the compounds of the invention of formula I, either when the ligand L is present as free base or as a salt and m is the integer 1, the platinum$^{II}$ atom is probably co-ordinated with the central nitrogen atoms of the aminoalkylamine side-chains. All the compounds of the invention are defined by elemental analyses in good agreement with the proposed formulae; the functional group present in the ligand molecule as well as the N-Pt interactions have been univocally determined by $^{13}$C—NMR, H—NMR, Pt-NMR and IR spectroscopy.

The univocal proof of the reported structures, still referred to as presumed structures, should only be possible through X-ray crystallographic investigation. Said analysis are not yet available because it was until now impossible to obtain crystals of the compounds I.

The invention, however, should not be intended as bounded in any way to the confirmation of the above reported hypothesis.

The structural hypothesis have however found indirect confirmation when, starting from possible ligands such as the compounds of formula III,

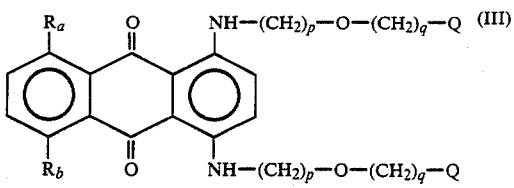

wherein $R_a$, $R_b$ and p are as above defined, Q is selected in the group consisting of H, lower alkyl and OH and the central atom of the aminoalkylamine chain is an oxygen atom instead of a nitrogen atom, it was impossible to form Pt$^{II}$ complexes, either in the cis or trans form, using the known experimental conditions.

This experimental failure further confirms that, in the compounds of formula III, when either $R_a$ and $R_b$ are hydrogen or hydroxy, the complex formation between the platinum atom and the aromatic amine functions of said ligands III is impossible. It is also impossible to obtain complex formation by coordination of the platinum atom with the quinone function and the adjacent amine or hydroxy functions.

Obviously, it follows that two central nitrogen atoms of the aminoalkylamine side-chains are requested for the coordination of the platinum atom in the compounds of formula I when m is the integer 1. The spectral data indicate the cis nature of the complex.

Table 1 shows the results obtained from a first experiment where the compounds cis-[1,4-bis-[2-(2-hydroxyethylamino)ethylamino]-5,8-dihydroxy-9,10-anthracenedione. Pt(DMSO)Cl$_2$].2HCl.H$_2$O (coded BBR 1651), water soluble, and cis-[1,4-bis-[2-(2-hydroxyethylamino)ethylamino]-5,8-dihydroxy-9,10-anthracenedione.PtCl$_2$].2HCl.H$_2$O (coded BBR 1734) are tested in comparison with equimolecular dosages of 1,4-bis-[2-(2-hydroxyethylamino)ethylamino]-5,8-dihydroxy-9,10-anthracenedione (DHAQ.2HCl) and with c-DDP dosed at 7 mg/kg, against L-1210 leukemia in mice. Groups of 10 animals, treated with intraperitoneal injections of $3.10^{-6}$ L-1210 cells, have been used at each dosage level, evaluating T/C percentage and long term survival, i.e. more than sixty days.

T/C percentage represents the percentual ratio of the mean survival time of the treated animals in comparison with the mean survival time of the control animals according to the methods described in "Anthracycline antibiotics" H. S. E. R Rhadem Edit., Academic Press, 1982.

LTS represents number of long-term (over 60 days) surviving animals with no pathologic episodes (i.e. cured animals).

A percentage of T/C over 120 indicates antitumoral activity; a percentage of T/C under 85 indicates toxicity. In some cases a LTS of 7/10 does not allow to evaluate the T/C percentage; in fact, any calculated value for the mean time should not be significative.

TABLE 1

| Substance | mg/kg | moles × $10^{-6}$ kg | % T/C | Survival after 60 days |
|---|---|---|---|---|
| BBR 1734 | 1.55 | 1.93 | 200 | 0/10 |
| | 3.10 | 3.86 | 224 | 1/10 |
| | 6.20 | 7.73 | n.e. | 7/10 |
| BBR 1651 | 1.85 | 1.93 | 195 | 0/10 |
| | 3.70 | 3.86 | 220 | 1/10 |
| | 7.40 | 7.73 | n.e. | 7/10 |
| DHAQ.2 HCl | 1.00 | 1.93 | 185 | 0.10 |
| | 2.00 | 3.86 | 214 | 0/10 |

TABLE 1-continued

| Substance | mg/kg | moles × $10^{-6}$ kg | % T/C | Survival after 60 days |
|---|---|---|---|---|
|  | 4.00 | 7.73 | 235 | 2/10 |
| c-DDP | 7.00 | 21 | 200 | 0/10 |

Both the compounds of the invention BBR 1651 and BBR 1734 show good activities with better results than those obtained using the known c-DDP and the aminoanthracenedione ligand alone.

In Table 2 a second experiment is reported, where the compound BBR 1651 is compared with c-DDP and the ligand DHAQ-2HCl in a L-1210 leukemia sensitive to cis-platinum (c-DDP). The results for the same compound in an animal model of L-1210 cis-platinum resistant leukemia are shown in Table 3.

TABLE 2

| | L-1210 Leukemia sensitive to c-DDP | | | | |
|---|---|---|---|---|---|
| | Doses | | | LTS (2) | |
| Drug | $10^{-6}$ moles/kg | mg/kg | T/C (1) % | (>60 days) | TOX (3) |
| c-DDP | 21 | 7.1 | 193 (187–200) | 0/20 | 0/20 |
|  | 29.2 | 10.0 | 93 (87–100) | 1/20 | 14/20 |
|  | 42 | 14.0 | 92 | 0/10 | 9/10 |
| DHAQ.2HCl | 1.93 | 1.0 | 185 | 0/10 | 0/10 |
|  | 3.86 | 2.0 | 214 | 0/10 | 0/10 |
|  | 7.73–8.68 | 4.0–4.5 | 302 (235–369) | 8/20 | 2/20 |
|  | 12.93 | 6.7 | 262 | 4/10 | 5/10 |
|  | 19.3 | 10.0 | 231 | 1/10 | 9/10 |
| BBR 1651 | 1.93 | 1.85 | 200 | 0/10 | 0/10 |
|  | 3.86 | 3.7 | 221 | 1/10 | 0/10 |
|  | 7.73–8.68 | 7.4–8.32 | N.E. | 15/20 | 0/20 |
|  | 12.93 | 12.40 | N.E. | 9/10 | 0/10 |
|  | 19.3 | 18.5 | N.E. | 9/10 | 0/10 |

(1) T/C: Mean survival time of treated mice/mean survival time of control (untreated) mice × 100. Mean survival time of treated mice is referred to dying animals only.
N.E. not evaluable as a consquence of the elevated number of alive animals (in parenthesis: range).
(2) LTS: Long-term survivors (>60 days), i.e. cured animals. Mean survival time of control animals: 8–10 days.
(3) TOX: Toxic deaths are referred to animals dead before control animals or to animals showing macroscopic toxic symptoms without tumor.

TABLE 3

| | c-DDP resistant L-1210 leukemia | | | | |
|---|---|---|---|---|---|
| | Doses | | | | |
| Drug | mg in $10^{-6}$/kg | mg/kg | T/C (1) % | LTS (2) (>30 days) | TOX (3) |
| DHAQ-2HCl | 5.79 | 3.0 | 145 | 1/10 | 0/10 |
|  | 8.68 | 4.5 | 168 | 2/10 | 0/10 |
| BBR 1651 | 19.3 | 18.5 | 186 | 3/10 | 0/10 |
|  | 28.95 | 27.75 | N.E. | 4/10 | 1/10 |
| c-DDP | 21 | 7.1 | 100 | 0/10 | 0/10 |
|  | 29.6 | 10.0 | 100 | 0/10 | 1/10 |

(1) T/C: Mean survival time of treated mice/mean survival time of control (untreated) mice × 100. Mean survival time of treated mice is referred to dying animals only. N.ev.: not evaluable as consequence of the elevated number of survivor animals.
(2) LTS: Long-terms survivors (>30 days), i.e. cured animals. Mean survival time of control animals: 8–10 days.
(3) TOX: Toxic deaths are referred to animals dead before control animals or to animals showing macroscopic toxic symptoms without tumor.

The results further confirm the great activity of the compounds of the invention.

In particular, the compound BBR 1651 is extremely more active than the known c-DDP and, even more surprisingly, its potency seems unrelated with an intrinsic toxicity. This is again more evident when the experimental data are evaluated on the basis of the platinum content (g/atom of Pt administered for kg of body weight). The molecular weights of c-DDP and of BBR 1651 are respectively 300.2 and 957.8; then, after administration of equiponderal doses of the two substances, the toal amount of platinum metal available for the interaction with DNA in the action sites is in a 3:1 ratio in favour of cis-platin.

In the first type of experiment (Table 2) cis-platin gives a T/C percentage ratio of 193 after a treatment with a dose equivalent to $21 \cdot 10^{-6}$ g/atom of Pt for kg of body weight. A T/C of 200 was measured for BBR 1651, administered at $1.39 \cdot 10^{-6}$ g/atom, i.e. after a dosage (platinum content) ten times smaller. Therefore, with an equal platinum content, the compound BBR 1651 allowed 9 longterms survivors (>60 days; i.e. cured animals) not allowing the evaluation of the T/C percentage value because of th surprising survival of such a high number of animals over 60 days. Accordingly, it was also impossible to calculate a significant value of the median time.

In animal treated with a dose of $29.6 \cdot 10^{-6}$ g/atom of Pt/kg of body weight (Table 2), 14 animals out of 20 died before the control animals, as a consequence of the intrinsic toxicity of the drug. Comparative data for BBR 1651 (0.10 at $19.3 \cdot 10^{-6}$ g/atom) are not available.

In the experiment of Table 3, where the animals were injected with cis-platin resistant leukemia cells, the two compounds possess similar toxicity, but, once again, BBR 1651 proves to be an active drug whereas cis-platin is uneffective.

On the other hand, the activity of the novel cis-platinum complex BBR 1651 cannot be considered related to its content in DHAQ. In fact, if equimolecular doses of the two compounds (BBR 1651 and DHAQ) are compared ($8.7 \cdot 10^{-6}$ mol/kg), BBR 1651 gave a 90% percentage of survivors at 60 days whereas DHAQ alone gave only a 10% survival percentage. Higher doses of DHAQ proved to be toxic, with an increase of death rate (up to 90%) in comparison with the control animals.

On the contrary, BBR 1651 treatment did not cause any increase of the dead animals before control animals.

The data reported in Table 2 are the means of two subsequent experiments.

Acute toxicity ($LD_{50}$) in mouse by intraperitoneal route was evaluated for two representative compounds of the invention, i.e. BBR 1734 and cis-[1,4-bis-[2-(2-hydroxyethylamino-ethyl)-amino]-9,10-anthracenedione.$PtCl_2$].$2HCl.H_2O$ (coded BBR 1775), in comparison with c-DDP.

| Acute toxicity in mouse i.e. mg/kg | |
| --- | --- |
| BBR 1734 | 22.9 |
| BBR 1735 | 30.0 |
| c-DDP | 17 |

20 Animals were treated by i.v. route with BBR 1734, BBR 1735 and c-DDP doses corresponding to the respective $LD_{50}$ values; a control group (20 animals) received the solvent only.

The percent decrease of the body weight, the kidney weight and the ureic nitrogen excretion were determined for each treated group. The increase of kidney weight and the increase of ureic plasma content were assumed as nephrotoxic index of the compounds (see for example O. Tofanetti et al., "Tumori", 69, 105, 1983).

The results are reported in Table 4.

TABLE 4

| Compounds | Initial body weight | Final body weight | % Δ of the body g/100 of body weight | Kidney weight | Kidney weight g/100 of body weight | Ureic Nitrogen (*) |
| --- | --- | --- | --- | --- | --- | --- |
| BBR 1734 | 34.2 ± 0.731 | 28.4 ± 0.775 | −20.4 | 0.362 ± 0.012 | 1.282 ± 0.036 | 14.85 ± 0.866 |
| BBR 1735 | 34.9 ± 0.857 | 33.1 ± 1.103 | −5.4 | 0.428 ± 0.02 | 1.293 ± 0.042 | 14.88 ± 0.565 |
| c-DDP | 36.6 ±1.397 | 27.3 ± 1.108 | −34.1 | 0.373 ± 0.009 | 1.407 ± 0.056 | 158.93 ± 38.72 |
| Controls | 28 ± 1.567 | 28.9 ± 1.784 | +3.1 | 0.373 ± 0.034 | 1.217 ± 0.08 | 23.45 ± 0.602 |

(*) Urea content in 100 mg/ml of plasma.

All the compounds negatively affects the increase of the body weight but c-DDP is significantly toxic.

The toxic effect of c-DDP is also clear and evident at the renal level, as shown by the relative increase of the kidney weight and by the damage of the excretory renal function with an increase of almost a logarythmic order of plasma ureic nitrogen.

On the other hand, the compounds BBR 1734 and BBR 1735, even if they show a general toxicity as indicated by the decrease of the body weight, do not impair the renal excretory function and/or change the relative kidney weight when tested at dosage levels which are letal for half of the treated animals.

These results are particularly relevant considering that similar T/C percentage of 200 is obtained with 7 mg/kg of c-DDP, with 1.55 mg/kg and with 8 mg/kg of BBR 1734 and BBR 1735 respectively, in the L-1210 leukemia (sensitive to Pt) test in the mouse, i.e. with a g/atom platinum content remarkably lower for the compounds of the invention (BBR 1734 and BBR 1735) in comparison with c-DDP.

The above described experimental data show that the compounds of the present invention are representative of a new class of compounds not strictly correlated with c-DDP, as well as with cytotoxic amino alkylamino anthracenediones.

It is noteworthy that the most active compounds of the invention are unexpectedly the charged complexes.

As a consequence, the compounds of the invention can be administered to humans in amounts ranging from about 0.05 mg to about 200 mg per square meter of body surface area per-day.

A preferred dosage regimen for optimal results would be from about 20 mg/m²/day to about 125 mg/m²/day.

For a patient of about 70 kg of body weight, the dosage ranging from about 0.4 mg to about 420 mg is administered in a 24 hour period.

This dosage regimen may be adjusted to provide the optimal therapeutic response. For example, the total dose may be administered in divided subdoses daily.

The dose may be proportionally reduced as a consequence of the particular therapeutic situation. The active compound may be administered by the intravenous, intramuscular or subcutaneous route; alternative administration ways are intraperitoneal and rectal routes.

The therapeutic dose can also be administered in alternate days and for two consecutive days followed by three or more days without medical treatment.

A therapeutic use of the novel compound by oral route is also possible using dosage levels 3-10 times higher than the parenteral optimal dose.

The compounds of the invention can also be used in proper experimental protocols of polychemotherapy in combination with other antineoplastic drugs such as anthracyclines, cyclophosphamide, bleomycine and vinblastine.

The compounds of the present invention can be used to treat tumors susceptible to platinum II treatment, including, for instance, tumors of the ovaries, testes, and kidneys, tumors of the head and neck, and lung tumors, as well as lymphomas, teratomas, sarcomas and mesotheliomas.

The pharmaceutical and veterinary compositions containing the compounds of the invention are prepared according to conventional methods and with conventional diluents and carriers.

For example, for intravenous injection or infusion sterile aqueous isotonic solutions are preferred; for subcutaneous or intramuscular injection, sterile solutions or suspensions in aqueous or non aqueous medium may be used.

For these purposes, instant preparations are preferably used, to be prepared immediately before the use starting from conventionally prepared lyophilized ampoules.

The following examples further illustrate but do not limit the present invention.

EXAMPLE 1

Under an inert gas atmosphere a solution of potassium tetrachloroplatinate (0.83 g) in water (50 ml) is added to a stirred solution of 1,4-bis-[2-(2-hydroxyethylamino)ethylamino]-5,8-dihydroxy-9,10-anthracenedione.2HCl (0.5 g) in water (300 ml). The mixture is kept at room temperature for 30 minutes and then the crystalline precipitate is filtered, washed with deionized water and dried under vacuum, to give 0.72 g of cis-[1,4-bis-[2-(2-hydroxyethylamino)ethylamino]-5,8-dihydroxy-9,10-anthracenedione.PtCl$_2$]-.2HCl.H$_2$O, m.p. 220° C.

Elemental analysis: for $C_{22}H_{32}Cl_4N_4O_7Pt$ (M.W. 801.05) calc.% C, 32.97; H, 4.02; Cl, 17.69; N, 6.99; O, 13.97; Pt, 24.34. found% C, 32.66; H, 4.04; Cl, 17.44; N, 6.88; O, 14.55; Pt, 24.18.

IR: 321 cm$^{-1}$ (shoulder 325-342 cm$^{-1}$: Pt-Cl).

NMR (DMSO-d$^6$, TMS): 3–4 (m, 16H); 7.63 (s, 2H); 7.8 (s, 2H); 9.06 (br s, 4H); 10.37 (t, 2H); 13.40 (s, 2H).

EXAMPLE 2

A solution of 0.1 g of the compound obtained using the procedure of the Example 1 in DMSO (2.1 ml) is kept for 3 hours at room temperature in inert gas atmosphere.

The excess DMSO is evaporated under high vacuum and the residue, after drying at 0.1 mm/kg for 12 hours, is crystallized from ethylether/pentane obtaining a crystalline powder melting at 250° C.: cis-[1,4-bis-[2-(2-hydroxyethylamino)ethylamino]-5,8-dihydroxy-9,10-anthracenedione.Pt(DMSO)$_2$Cl$_2$].2HCl.H$_2$O.

Elemental analysis: for C$_{26}$H$_{44}$Cl$_4$N$_4$O$_9$PtS$_2$ (M.W. 957.83) calc. % C, 32.60; H, 4.63; N, 5.84. found % C, 31.81; H, 4.06; N, 5.91.

EXAMPLE 3

Under argon atmosphere and in the dark, a potassium tetrachloroplatinate solution (0.456 g) in water (20 ml) is added dropwise to a stirred solution of 1,4-[bis-[2-(2-hydroxyethylamino)ethylamino]-9,10-anthracenedione.2HCl (0.407 g) in water (20 ml). The stirring is continued for 3 hours at room temperature, then the crystalline precipitate is removed by centrifugation, washed with 2×10 ml of water and 2×20 ml of ethanol, dried under high vacuum for a night to give 0.7 g of 1,4-[bis-[2-(2-hydroxyethylamino)ethylamino]-9,10-anthracenedione.PtCl$_2$].2HCl.H$_2$O with a 91% yield.

Elemental analysis: for C$_{22}$H$_{32}$N$_4$O$_5$Cl$_4$Pt (M.W. 768.41) calc.% C, 34.34; H, 4.19; N, 7.28; Cl, 18.45; Pt, 25.35. found % C, 34.42; H, 4.16; N, 7.19; Cl, 18.20; Pt, 25.06.

IR: 325 cm$^{-1}$ (shoulder) 315 cm$^{-1}$: Pt-Cl. The other frequencies are identical to those of the free ligand.

NMR (DMSO-d$^6$, TMS): 3–4 (m, 16H); 7.64 (s, 2H); 7.8–8.3 (m, 4H); 10.6 (s, 2H).

Using a molar excess of potassium chloroplatinate, the 1:1 ratio between ligand and platinum atom does not change.

EXAMPLE 4

A NaHCO$_3$ solution (0.024 g) in water (5 ml) is added under inert gas atmosphere to a suspension of 0.1 g of the compound prepared according to the procedure of the Example 3, in 5 ml of water.

After stirring overnight, a second portion of NaHCO$_3$ is added (0.014 g) and the mixture is further stirred for 6 hours.

The solid is filtered, washed with water (2×5 ml) and ethanol (3 ml) and dried under high vacuum to give 0.079 g of cis-[1,4-bis-[2-(2-hydroxyethylamino)ethylamino]-9,10-anthracenedione.PtCl$_2$].H$_2$O.

Elemental analysis: for C$_{22}$H$_{30}$N$_4$O$_5$Cl$_2$Pt (M.W. 696.1) calc. % C, 37.92; H, 4.31; N, 8.04. found % C, 38.07; H, 4.21; N, 7.98.

IR: 326 cm$^{-1}$ Pt-Cl

NMR (DMSO-d$^6$, TMS): 2.8–4 (m, 18H); 5.05 (m, 2H); 7.62 (s, 2H); 7.7–8.4 (m, 4H); 10.7 (m, 2H).

EXAMPLE 5

Under inert gas atmosphere and with protection from sun light, a potassium tetrachloroplatinate solution (0.25 g) in water (10 ml) is added to a solution of 1,4-bis-(2-(2-hydroxyethylamino)ethylamino)-9,10-anthracenedione (0.2 g) in dimethylformamide (40 ml). The mixture is stirred for 8 hours at room temperature and the blue precipitate is collected by filtration and then stirred in deionized water (50 ml), filtered, washed with ethanol and dried under vacuum to give 0.31 g of a compound corresponding to the complex obtained in the Example 4.

EXAMPLE 6

An aqueous potassium tetrachloroplatinate solution (0.43 g in 10 ml) was added to a solution of 1,4-bis-[2-(2-N-morfolinoethyl)-amino]-5,8-dihydroxy-9,10-anthracenedione.2HCl (0.351 g) in water (80 ml).

Under protection from sunlight and under inert gas atmosphere, the mixture is stirred for 21 hours. The solid precipitate is removed by centrifugation, stirred for three times with water (40 ml) and then with ethanol (30 ml) to give, after drying under vacuum, 0.418 g of cis-[1,4-[2-[N-morpholinoethyl]amino]-5,8-dihydroxy.PtCl$_2$].2HCl (81% yield).

Elemental analysis: for C$_{26}$H$_{34}$O$_6$N$_4$Cl$_4$Pt (M.W. 835.1) calc.% C, 37.36; H, 4.07; N, 6.70; Cl, 17.00; Pt, 23.36. found% C, 37.20; H, 3.99; N, 6.65; Cl, 17.10; Pt, 23.48.

IR: 325 cm$^{-1}$ (shoulder) Pt-Cl.

Using in this procedure the corresponding anthracenedione ligands, the following complexes are prepared:

cis-[1,4-bis-[2-(N-piperidyl)ethylamino]-5,8-dihydroxy-9,10-anthracenedione.PtCl$_2$].2HCl.H$_2$O;

cis-[1,4-bis-[2-(N-piperidyl)ethylamino]-9,10-anthracenedione.PtCl$_2$].2HCl.H$_2$O;

cis-[1,4-bis-[2-(N-pyrrolidyl)ethylamino]-5,8-dihydroxy-9,10-anthracenedione.PtCl$_2$].2HCl.H$_2$O;

cis-[1,4-bis-[2-(N-propylamino)ethylamino]-5,8-dihydroxy-9,10-anthracenedione.PtCl$_2$].3HCl.H$_2$O;

cis-[1,4-bis-[2-(2-hydroxyethylamino)propyl]-5,8-dihydroxy-9,10-anthracenedione.PtCl$_2$].2HCl.

EXAMPLE 7

By adding an aqueous potassium tetrachloroplatinate solution (0.41 g in 10 ml) to a solution of 1,4-bis-[2-aminoethylamino]-9,10-anthracenedione, under inert gas atmosphere and sun light protection, after stirring for 21 hours at r.t. and usual work-up followed by dispersion in ethanol-water (1:1, 25 ml) and final crystallization from ethanol, 0.41 g of pure cis-[1,4-bis-[2-aminoethylamino]-9,10-anthracenedione.PtCl$_2$].½EtOH is prepared.

Elemental analysis: for C$_{19}$H$_{23}$O$_{2.5}$N$_4$Cl$_2$Pt (M.W. 613.1) calc.% C, 37.18; H, 3.75; N, 9.13; Cl, 11.58; Pt, 31.83. found% C, 36.97; H, 3,84; N, 9.23; Cl, 11.34; Pt, 31.36.

IR: 326 and 320 cm$^{-1}$—Pt-Cl.

EXAMPLE 8

An aqueous potassium tetrachloroplatinate solution (1.9 g/100 ml) is added to a solution of a 1,4-bis-[2-(2-hydroxyethylamino)-5,8-dihydroxy-9,10-anthracenedione.2HCl (1.05 g) in water (680 ml), in one hour and under argon atmosphere, under vigorous stirring and in the dark. The mixture is further stirred for two hours, then it is left to stand for 30 minutes. The crystalline precipitate is filtered, washed with deionized water until Cl ions disappear from eluate, then it is dried under high vacuum, protected from sunlight, to give 1.32 g of cis-[1,4-bis[2-(2-hydroxyethylamino)ethylamino]-5,8-dihydroxy-9,10-anthracenedione.PtCl$_2$].2HCl.H$_2$O, m.p. 221°–222° C.

Elemental analysis for $C_{22}H_{32}Cl_2N_4O_7Pt$ (M.W. 801.05) calc.% C, 32.97; H, 4.02; Cl, 17.69; N, 6.99; O, 13.97; Pt, 24.34. found% C, 32.72; H, 4.03; Cl, 17.54; N, 6.87; O, 14.15; Pt, 24.28.

IR: 321 cm$^{-1}$ (shoulder, 325-342 cm$^{-1}$ Pt-Cl).

In the region 1700-600 cm$^{-1}$ the IR spectrum is substantially unchanged in comparison with the IR spectrum of ligand, showing that the hydroquinone substructure is the same in both the compounds.

H-NMR (DMSO-d$_6$, TMS): 3-4 (m 16H); 7.63 (s, 2H); 7.8 (s, 2H), 9.06 (br s, 4H); 10.37 (t, 2H); 13.40 (s, 2H).

A solution of the compound in DMSO-d$^6$ shows in 195 Pt-NMR a signal at $-2962$ with respect to the signal of the $PtCl_6^{2-}$.

After five days, the 195 Pt-NMR does not show further modifications.

$^{13}$C-NMR (DMSO-d$_6$, TMS): 84; 154. 145; 125; 124; 114; 108; 56; 49; 46; 38. (21 ppm).

These signals are not significantly changed in comparison to the signals of the free ligand.

In inert gas atmosphere and in the dark, a suspension of 0.58 g of said micronized complex in deionized and disaerated water, is kept for 36 hours under stirring and sonication.

The solid in suspension is filtered to give a material whose elemental analysis is in agreement with the structure of bis-[2-(2-hydroxyethylamino)ethylamino]-5,8-dihydroxy-9,10-anthracenedione.PtCl$_{1.5}$OH$_{0.5}$].2HCl.H$_2$O.

Elemental analysis: for $C_{22}H_{32.5}N_4O_{7.5}Cl_{3.5}Pt$ (M.W. 791.85) calc.% C, 33.33; H, 4.10; N, 7.07; O, 15.15; Cl, 15.69; Pt, 24.64. found% C, 33.43; H, 4.05; N, 7.05; O, 15.28; Cl, 15.40; Pt, 24.69.

IR: 323 cm$^{-1}$ and shoulder 315 cm$^{-1}$ Pt-Cl.

The filtered solution is concentrated up to 20 ml by lyophylization and then it is diluted with ethanol to give, as crystalline solid (0.17 g), cis-[1,4-bis-[2-(2-hydroxyethylamino)ethylamino]-5,8-dihydroxy-9,10-anthracene dione.PtClOH].2HCl.0.5.H$_2$O.0.5.EtOH.

Elemental analysis: for $C_{23}H_{35}N_4O_8Cl_3Pt$ (M.W. 791.147) calc.% C, 34.65; H, 4.39; N, 7.02; O, 16.05; Cl, 13.34; Pt, 24.48. found% C, 34.58; H, 4.41; N, 7.04; O, 16.01; Cl, 13.27; Pt, 24.52.

IR: 315 cm$^{-1}$ with shoulder at 325 cm$^{-1}$ Pt-Cl.

The IR spectrum in the 1800-450 cm$^{-1}$ is unchanged in comparison to the ligand, and in particular the hydroxyquinone substructure is the same in both the compounds.

Using in this procedure the platinum complex of Example 3 the following aquo complex is prepared: cis-[1,4-bis-[2-(2-hydroxyethylamino)ethylamino]-9,10-anthracenedione.PtClOH].2HCl.H$_2$O.

EXAMPLE 9

An aqueous potassium tetrachloroplatinate solution (0.46 g) in water (18 ml) is added under stirring to a solution of 1,4-bis-[2-(2,2-dimethyl-oxazolidinyl)ethylamino]-9,10-anthracenedione (m.p. 159°-160° C., 0.5 g) in dimethylformamide. After stirring for 24 hours and usual work-up 0.53 g of cis-[1,4-bis-[2-(2-hydroxyethylamino)ethylamino]-9,10-anthracenedione.PtCl$_2$].-H$_2$O are obtained. The oxazolidine ring is cleaved during the complex formation. The compound corresponds to the compounds obtained in the Example 3 and 4.

EXAMPLE 10

0.92 Grams of the cis-[1,4-bis-[2-(2-hydroxyethylamino)ethylamino]-9,10-anthracenedione.PtCl$_2$].2HCl.H$_2$O (prepared using the procedure of Example 3) is dissolved in dry DMSO (25 ml). The solution, protected from sunlight and moisture, is kept for five days under argon atmosphere at 18°-20° C., then it is diluted with purified ethylacetate.

A crystalline precipitate is separated, filtered and washed with ethylacetate and purified from CH$_2$Cl$_2$—HCOH to give 0.42 g of cis-[1,4-bis-[2-(2-hydroxyethylamino)ethyamino]-9,10-anthracenedione.Pt(DMSO)$_2$Cl$_2$].2HCl.H$_2$O.

Elemental analysis: $C_{26}H_{44}N_4O_7S_2Cl_4Pt$ (M.W. 925.826) calc.% C, 33.72; H, 4.79; O, 12.09; S, 6.92; Cl, 15.31; Pt, 21.08. found% C, 33,81; H, 4.72; O, n.d.; S, 6.98; Cl, 15.16; Pt, 21.17.

Using in this procedure the platinum complexes prepared in accordance with the procedure of Example 6, the following compounds are obtained:

cis-[1,4-bis-[2-(N-morpholinoethyl)amino]-5,8-dihydroxy-9,10-anthracenedione.Pt(D-MSO)$_2$Cl$_2$].2HCl;

cis-[1,4-bis-[2-hydroxyethylamino)ethylamino]-5,8-dihydroxy-9,10-anthracenedione.Pt(DMSO)-2OHCl].2HCl.H$_2$O;

cis-[1,4-bis-[2-hydroxyethylamino)ethylamino]-5,8-dihydroxy-9,10-anthracenedione.Pt(D-MSO)$_2$Cl$_2$].2HCl.H$_2$O.

EXAMPLE 11

1,4-Bis-[2-(2-hydroxyethylamino)ethylamino]-5,8-dihydroxy-9,10-anthracenedione (1 g) is dissolved in hot 2-methoxyethanole (60 ml). The solution is cooled at 15°-18° C. and filtered. In inert gas atmosphere, a solution of [PtCl$_2$(CH$_3$CN)$_2$] (0.80 g) is added to the filtrate in acetonitrile (15 ml) and the mixture, protected from sunlight, is stirred for 24 hours at room temperature.

The crystalline precipitate is filtered, micronized and treated with water (25 ml). The mixture is stirred for 2 hours and filtered to give cis-[1,4-bis-[2-(2-hydroxyethylamino)ethylamino]-5,8-dihydroxy-9,10-anthracenedione.PtCl$_2$].½H$_2$O.

We claim:

1. A cis-platinum complex of formula I $$\text{cis-[L-(Pt}^{II}\text{XX')].(Solv)}_n \qquad (I)$$

wherein

X and X', which can be the same or different, are a ligand selected from the group consisting of Cl, OH, CH$_3$SOCH$_3$.Cl, CH$_3$SOCH$_3$.OH;

n is zero or ½ or an integer from 1 to 6;

solv represents a crystallization solvent selected from the group consisting of water, a lower C$_1$-C$_5$ alcohol, acetonitrile or ethylacetate and L is a bidentate ligand selected from the group of 1,4-diamino-9,10-anthracenedione of formula II

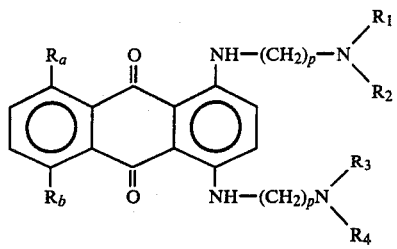 (II)

wherein
 each of $R_a$ and $R_b$, which are the same or different, are hydrogen or hydroxy;
 $R_1$, $R_2$, $R_3$ and $R_4$, which are the same or different, are hydrogen, $C_1$–$C_5$ lower alkyl or —$(CH_2)_{p1}$—OH;
 p and p1 are, independently, the integer 2 or 3; or at least one of $R_1$, $R_2$ and $R_3$, $R_4$ respectively, taken together with the nitrogen atom to which they are connected independently forms an hetercyclic ring having the formula

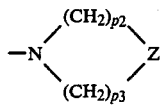

wherein Z is —$CH_2$— or O, while p2 and p3 are independently 1 or 2, and a salt of said ligand L with pharmaceutically and veterinary acceptable acids; wherein the two central nitrogen atoms of the aminoalkylamine side-chains are coordinated with said platinum$^{II}$ atom.

2. A compound according to claim 1, wherein X and X' are Cl.

3. A compound according to claim 1, wherein X is Cl and X' is OH.

4. A compound according to claim 1, wherein X and X', each which can be the same or different, are $CH_3SOCH_3$. Cl or $CH_3SOCH_3$.OH.

5. A compound according to claim 1, wherein p is 2 and one of $R_1$ and $R_2$, and $R_3$ and $R_4$, respectively, is 2-hydroxyethyl.

6. Compound of claim 5, wherein each of $R_a$ and $R_b$ are hydrogen.

7. A complex of claim 1 selected from the group consisting of:
 cis-[1,4-bis-[2-(2-hydroxyethylamino)ethylamino]-5,8-dihydroxy-9,10-anthracene-dione.PtCl$_2$_].2HCl;
 cis-[1,4-bis-[2-(2-hydroxyethylamino)ethylamino]-5,8-dihydroxy-9,10-anthracenedione.Pt(DMSO)$_2$Cl$_2$].2HCl.H$_2$O;
 1,4-[bis-[2-(2-hydroxyethylamino)ethylamino-9,10-anthracenedione.PtCl$_2$].2HCl.H$_2$O;
 cis-[1,4-bis-[2-(2-hydroxyethylamino)ethylamino]-9,10anthracenedione.PtCl$_2$].H$_2$O;
 cis-[1,4-bis-[2-[N-morpholinoethyl]amino]-5,8-dihydroxy.PtCl$_2$].2HCl;
 cis-[1,4-bis-[2-(N-pyrrolidyl)ethylamino]-5,8-dihydroxy-9,10-anthracenedione.PtCl$_2$].2HCl$_2$.H$_2$O;
 cis-[1,4-bis-[2-(2-hydroxyethylamino)ethylamino]-5,8-dihydroxy-9,10-anthracenedione.PtCl$_2$].2HCl.-H$_2$O;
 cis-[1,4-bis-[2-(2-hydroxyethylamino)ethylamino]-5,8-dihydroxy-9,10-anthracenedione.Pt-ClOH].2HCl.0.5.H$_2$O.0,5.EtOH;
 cis-[1,4-bis-[2-(2-hydroxyethylamino)ethylamino]-9,10-anthracenedione.PtClOH].2HCl.H$_2$O;
 cis-[1,4-bis-[2-(2-hydroxyethylamino)ethylamino]-9,10-anthracenedione.Pt(DMSO)$_2$Cl$_2$].2HCl.-H$_2$O;
 cis-[1,4-bis-[2-(2-(N-morpholinoethyl)amino]-5,8-dihydroxy-9,10-anthracenedione.Pt(D-MSO)$_2$Cl$_2$].2HCl;
 cis-[1,4-bis-[2-hydroxyethylamino)ethylamino]-5,8-dihydroxy-9,10-anthracenedione.Pt(DMOS)-$_2$OHCl.2HCl.H$_2$O;
 cis-[1,4-bis-[2-hydroxyethylamino)ethylamino]-5,8-dihydroxy-9,10-anthracenedione.Pt(D-MSO)$_2$Cl$_2$].2HCl.H$_2$O.

8. Process for the preparation of compounds of general Formula I $$\text{cis-}[L\text{-}(Pt^{II}XX')].(Solv)_n \quad (II)$$

wherein
 X and X', which can be the same or different, are a ligand selected from the group consisting of Cl, OH, $CH_3SOCH_3$.Cl, $CH_3SOCH_3$.OH;
 n is zero or ½ or an integer from 1 to 6;
 solv represents a crystallization solvent selected from the group consisting of water, a lower $C_1$–$C_5$ alcohol, acetonitrile or ethylacetate and
 L is a bidentate ligand
  which is a 1,4-diamino-9,10-anthracenedione of Formula II as defined hereinafter,
 characterized in that a bidentate ligand of formula II

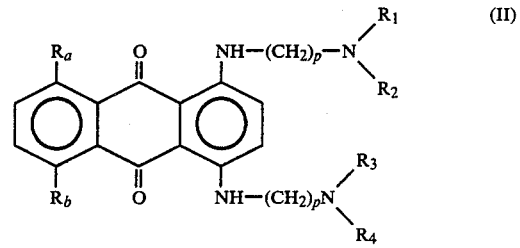 (II)

wherein
 each of $R_a$ and $R_b$, which are the same or different, are hydrogen or hydroxy;
 $R_1$, $R_2$, $R_3$ and $R_4$, which are the same or different, are hydrogen, $C_1$–$C_5$ lower alkyl or —$(CH_2)_{p1}$—OH;
 p and p1 are independently the integer 2 or 3; or at least one of $R_1$, $R_2$ and $R_3$, $R_4$ respectively, taken together with the nitrogen atom to which they are connected independently form a heterocyclic ring having the formula

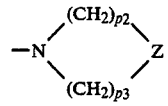

wherein
 Z is —$CH_2$— or O;
 and p2 and p3 are independently 1 or 2;
is reacted at room temperature with an equal molar amount of a Pt$^{II}$ compound selected from the group consisting of K$_2$PtCl$_4$ and PtCl$_2$CH$_3$CN in a suitable solvent selected from the group consisting of water, low molecular weight alcohols, dimethylformamide, acetonitrile and mixtures thereof.

9. Process of claim 8, including the further step of contacting the reaction product of claim 8 with dimethylsulphoxide until 1 to 2 moles of dimethylsulphoxide are inserted into the reaction product and are coordinated at the platinum atom.

10. Process of claim 8, wherein the bidentate ligand of formula II is in the salt form.

11. Reaction product produced by reacting at a temperature of 15° to 40° C. dimethylsulphoxide and the complex of claim 1.

12. Pharmaceutical composition for the treatment of a tumor susceptible to platinum$^{II}$ therapy in a patient in need of such treatment, said composition comprising an antitumoral effective amount of a complex of claim 1 and a pharmaceutically acceptable carrier therefor.

13. Composition of claim 12, wherein said compound is in a form suitable for peritoneal administration.

14. Composition of claim 12, wherein said composition is in a form suitable for oral administration.

* * * * *